United States Patent [19]

Adler et al.

[11] Patent Number: 4,870,673
[45] Date of Patent: Sep. 26, 1989

[54] DENTAL X-RAY INSTALLATION

[75] Inventors: Rolf Adler, Bensheim Fehlheim; Erich Heubeck; Manfred Muether, both of Bensheim, all of Fed. Rep. of Germany

[73] Assignee: Siemens Aktiengesellschaft, Berlin and Munich, Fed. Rep. of Germany

[21] Appl. No.: 102,551

[22] Filed: Sep. 29, 1987

[30] Foreign Application Priority Data

Sep. 30, 1986 [DE] Fed. Rep. of Germany ....... 3633252

[51] Int. Cl.$^4$ ................................................ G21K 1/02
[52] U.S. Cl. ........................................ 378/148; 378/38; 378/21; 378/39; 378/117
[58] Field of Search ..................... 378/38–40, 378/145, 147–148, 115, 117, 156–157, 181–187, 205

[56] References Cited

U.S. PATENT DOCUMENTS

| | | | |
|---|---|---|---|
| 581,199 | 4/1897 | Easton | 378/148 |
| 2,591,536 | 4/1952 | Gieringer et al. | 378/148 |
| 3,502,878 | 3/1970 | Stewart et al. | 250/105 |
| 3,631,249 | 12/1971 | Friede et al. | 378/148 |
| 3,643,095 | 2/1972 | Shuster | 250/105 |
| 3,875,411 | 4/1975 | Kunert | 250/402 |
| 3,947,689 | 3/1976 | Wagner | 250/512 |
| 3,986,034 | 10/1976 | Wittkopp et al. | 250/468 |
| 4,070,582 | 1/1978 | Kisrow | 378/98 |
| 4,121,104 | 10/1978 | Richter | 378/182 |
| 4,137,460 | 1/1979 | Fitzsimmons et al. | 378/117 |
| 4,195,229 | 3/1980 | Suzuki | 250/445 |
| 4,221,971 | 9/1980 | Burger | 378/148 |
| 4,232,227 | 11/1980 | Finkenzeller et al. | 378/181 |
| 4,277,685 | 7/1981 | Covic et al. | 378/156 |
| 4,606,063 | 8/1986 | Berghagen | 378/41 |
| 4,679,221 | 7/1987 | O'Brien et al. | 378/148 |
| 4,694,478 | 9/1987 | Delnor | 378/38 |
| 4,766,603 | 8/1988 | Okabe et al. | 378/162 |
| 4,788,699 | 11/1988 | Dobert et al. | 378/150 |

FOREIGN PATENT DOCUMENTS

| | | | |
|---|---|---|---|
| 0216287 | 4/1987 | European Pat. Off. | 378/182 |
| 3428747 | 2/1986 | Fed. Rep. of Germany | 378/182 |

OTHER PUBLICATIONS

Siemens sales brochure entitled "Minimize X-ray Dosage Maximize Image Quality . . . ", 1984.

Primary Examiner—Janice A. Howell
Assistant Examiner—John C. Freeman
Attorney, Agent, or Firm—Hill, Van Santen, Steadman & Simpson

[57] ABSTRACT

A dental x-ray diagnostics installation having a holder for film cassette and a holder for diaphragms of different sizes, which holder for diaphragms is positioned in an x-ray source so that the beam passes through the diaphragm aperture before reaching the subject. The diaphragms are interchangeable with one another and have different diaphragm apertures for the purpose of matching the x-ray beam cross-section to different film cassette formats. In order to be able to more easily execute exposures having film cassettes of different sizes, the installation of the present invention includes a sensing arrangement for determining the size and position of the format of each film cassette inserted into the holder, a logic circuit for taking the output of the sensing arrangement and directing it either to a display unit and/or to a control unit which controls the radiation source dependent on the selected film format and/or controls the adjustment mechanism for a diaphragm arrangement comprising a plurality of diaphragm apertures which are allocated to the different cassette formats.

6 Claims, 5 Drawing Sheets

DENTAL X-RAY INSTALLATION

BACKGROUND OF THE INVENTION

The present invention is direct to a dental x-ray diagnostics installation having a source of x-radiation and a holder for a film cassette with the source of x-radiation having a diaphragm for limiting the x-ray beam, which diaphragm is interchangeably held for the purpose of changing the diaphragm opening for different film cassette formats.

In panorama x-ray diagnostics installations with which slice exposures of the jaw of a patient can be produced, there is frequently the possibility of being able to produce exposures of the entire skull of a patient, which exposures are referred to as ceph exposures, with the assistance of an additional, adaptable head holder. Given a change from slice exposure to ceph exposure, it is necessary, for reasons of radiation protection, to limit the width or shape of the x-ray beam of the primary diaphragm to the cassette format. To this end, a known apparatus sold under the trademark "ORTHOPANTOMOGRAPH 10" has a unit sold under the trademark "ORTHOCEPH 10", and is provided with two primary diaphragms provided with different diaphragm openings for slice exposures on the one hand and for ceph exposures on the other hand. These primary diaphragms have to be interchanged when a switch is made from a slice exposure to a ceph exposure and vice versa.

Over and above the possibility of being able to alternatively select between slice exposure and ceph exposure, there is also a desire to be able to expose regions of the subject which differ in size, for example, portions of the skull or of the jaw. To this end, it can be appropriate to change the cassette format and to limit the radiation beam to the selected format for reasons of radiation protection.

SUMMARY OF THE INVENTION

The present invention is directed to providing an x-ray diagnostics installation wherein different film cassettes can be provided for different exposures. The object enables avoiding the involved manipulation so that there is no incorrect possible omission of high radiation doses in the output beam because of a change in the cassette format and, in particular that the primary diaphragm corresponds to the format of the selected cassette.

To achieve these goals, the present invention is directed to an improvement in a dental x-ray diagnostics installation having a holder for a film cassette and a holder for a diaphragm being provided between the radiation source and the subject being x-rayed, said diaphragm being interchangeable for another having a different diaphragm aperture for the purpose of changing the film cassette format. The improvements are that the film cassette holder includes sensing means which senses the position and format of the film cassette that is inserted in the holder to produce electrical signals, a logic circuit for editing the signals to produce an edit signal and means for utilizing the edit signal of the logic means. The means for utilizing can be a display unit, a control unit or a means which controls the radiation source dependent on the selected film format, or a control unit that controls and adjusts the diaphragm arrangement of a plurality of diaphragm apertures allocated for different formats. The means for utilizing can be either any one of the above or combinations thereof.

In the case of control of a radiation source, the logic circuit is preferably designed so that the signal from the sensor means, which corresponds to the selected film cassette format, is compared to signals from additional sensing means which is allocated to the diaphragm arrangement comprising a plurality of diaphragm apertures allocated to different formats. A check is, thus, undertaken in a comparison logic to see whether the proper diaphragm is allocated to the selected film cassette format. When this is not the case, the control unit remains interlocked or inactive to prevent actuation of the x-ray source. The x-ray source is only able to operate when the film cassette format and the diaphragm aperture correspond to each other. The selection or, respectively, the switching of the diaphragm can, thus, occur both manually as well as under a motordrive. In the case of a motor adjustment of the diaphragm, it is advantageous to provide a carrier for the diaphragm arrangement comprising a plurality of diaphragms, each exhibiting a different diaphragm aperture, and to control the carrier directly dependent on the selected film format.

The sensor arrangement can be composed of an optical arrangement comprising, for example, light-emitting diodes and photo elements or reflective light barriers which are arranged in the holder for the film cassette in accordance with the provided cassette format. Advantageously, the sensor means is arranged so that the outside edges of the film cassette are covered in at least one of the two dimension, such as width or height.

The sensor means can also be composed of an optical or a combination of optical, electrical and mechanical means. In accordance with the advantageous development of the invention, at least one pivotably seated sensing lever has one end pressing against a reference surface on the cassette, which surface defines the cassette and the pivoted position of the lever at insertion of the cassette is determined by light barriers. Alternatively, the pivotably seated sensing lever can also be coupled to a potentiometer, wherein different values of the resistance occur for different pivoted positions corresponding to the film cassette format and the analog signals of these values of resistance are capable of being converted into a digital signal by an analog-to-digital converter.

Instead of potentiometers, optical angle generators can also be provided, for example in the form of sector disks connected to the sensing levers which move between light-emitting diodes and photodiodes.

The signals acquired from the sensor arrangement which, first, reveals that a film cassette is inserted into the holder and, second, supplies a size for the selected format can be supplied in a conventional processing technology to a comparator which compares the identified values to stored values and creates an output signal for a control unit which is provided for the purpose of appropriately adjusting the diaphragm arrangement which comprises a plurality of primary diaphragms exhibiting different apertures.

The editing and comparison of the signals can, advantageously, occur with integrated circuit technology.

The diaphragm arrangement can be differently constructed. For example, it can be composed of a carrier comprising all occurring diaphragm apertures which are arranged either for rotatable displacement or longitudinal displacement. The adjustable motor brings the selected diaphragm arrangement into the respective required position in the aforementioned way. Individual diaphragm elements can, likewise, be provided and these are brought into respectively required position on the basis of the corresponding adjustment mechanism.

The diaphragm arrangement can, advantageously, contain the aforementioned additional sensing means which reports diaphragm-associated information to the comparison logic.

Other advantages and improvements of the present invention will be readily apparent from the following description of the preferred embodiments, the drawings and claims.

DESCRIPTION OF PREFERRED EMBODIMENTS

Figure 1:
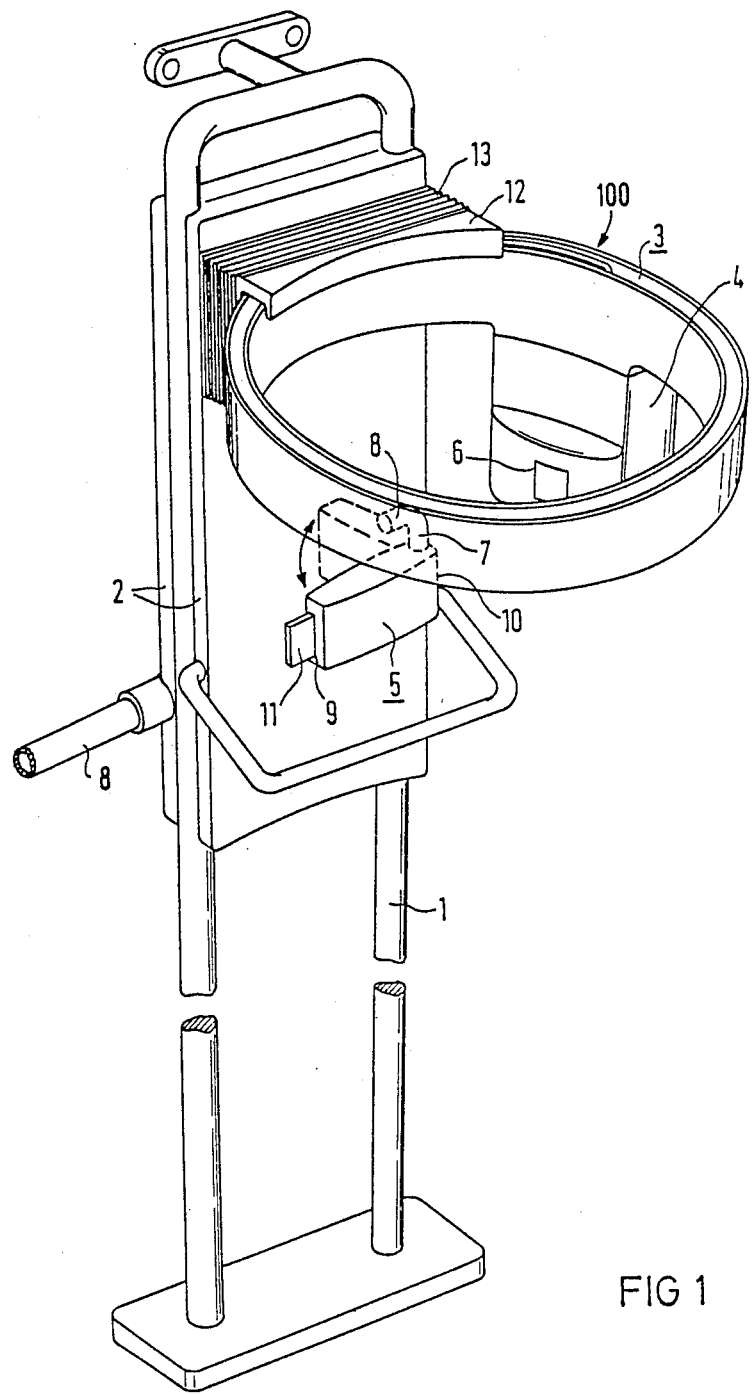
FIG. 1 is a perspective view of an x-ray diagnostics installation used with the present invention.

The principals of the present invention are particularly useful when incorporated in a dental x-ray diagnostics installation, generally indicated at 100 in FIG. 1. The diagnostics installation 100 contains a stand 1 formed by two upright pipes on which a carriage 2 is held in a height adjustable fashion. A rotational unit 3 in the form of a closed ring is held on the carriage, and this unit 3 carries an x-radiator 4 and diametrically opposite a film cassette holder 5. The x-radiator 4 is in a housing which has a beam exit opening 6. The film cassette holder 5 is mounted on the closed ring by an angled carrier arm 7, which enables the cassette to be pivoted in the direction shown by the double arrow. The film cassette holder can be, thus, brought from a used position, shown in broken lines, which is suitable for normal slice exposures, into a non-use position, shown in solid lines which, first, makes it easier for the assistant to position the patient's head to be arranged between the radiation source 4 and the film cassette holder 5 and, secondly, enables the production of remote exposures that are referred to as ceph exposures. In order to be able to make such remote exposures, head positioning means, generally indicated at 101 in FIG. 4, and a cassette holder means must be provided at a specific distance of about 1.5 m from the x-ray source 4. To support the head positioning means and cassette holder means, a carrier pipe 8 has one end connected to the carriage 2 and the other end connected to the positioning means 101 (see FIG. 4).

The film cassette holder 5 (FIG. 1), which is provided for the acceptance of normal slice photographs, contains a slotshaped admission and exit openings 9 and 10 on both ends of the cassette, through which a film cassette 11 can be introduced or, respectively, can be removed after exposure. The film cassette employed is a flexible film cassette provided with reinforcing foils, as fundamentally employed for intra-oral exposures. The transport of the film cassette occurs on the basis of an electromotive drive arranged in the film cassette holder 5, which is not shown in detail.

The rotary ring forming the rotational unit 3 is held rotatably in a bearing part 12, and is also pivotal relative to the carriage 2. The adjustment mechanism, which is not shown in detail required for this purpose is situated between the carriage 2 and the ring 3 and is covered by an accordion bellows 13. The adjustment mechanism enables the rotary ring and, thus, the position of the x-radiation source 4 and the film cassette holder 5 to be brought into any arbitrary position needed for orbit around a patient's head. The means for controlling the position and the movement are by appropriate adjustment motors, which are not shown. In combination with the autorotation, which the rotary ring can also execute around its center axis, and in combination with the film cassette, adjustability in the cassette holder 5, the motion sequence of the desired exposures can be correspondingly controlled.

Figure 2:
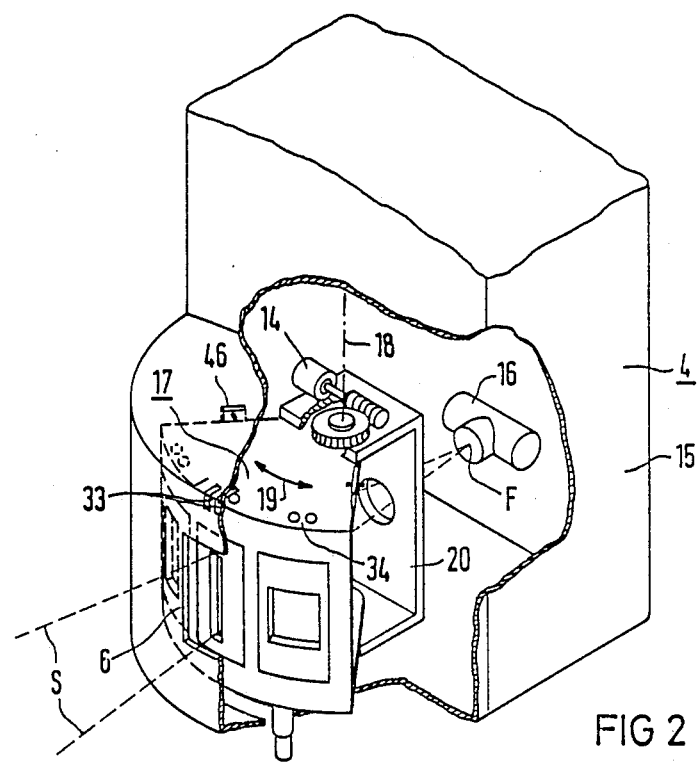
FIG. 2 is an enlarged, perspective view, with portions broken away for purposes of illustration, of the x-radiator or source of the present invention.

In FIG. 2, the x-radiator 4 is shown, with a housing 15 partially broken away. The x-radiator 4 includes an x-ray tube 16, which is the actual radiation source, and is arranged in a known way in the back part of the housing 15. The rays, referenced S, emerge from the radiation source and expose the film that is arranged in a film cassette 11 after transirradiating the patient's head. The focus of the ray beam proceeding from the tube 16 is accomplished by a focussing means F. A multiple diaphragm part 17 is provided in the beam path between the radiation source 16 and the window 6 of the housing 15, and this multiple diaphragm part 17 is held in the housing of the radiator to pivot on an axis of a journal bearing 18, as indicated by the double arrow 19. A retaining part 20, which is fashioned U-shaped, provides a corresponding opening for the passage of the radiation and provides the bearings for the diaphragm part 17. The multiple diaphragm part 17 is driven by a drive unit 14, which can be composed of a stepping motor with gearing in a known way, so that one of the plurality of diaphragm apertures of the multiple diaphragm part 17 can be aligned to the beam path of the radiator in a way as described hereinbelow.

Figure 3:
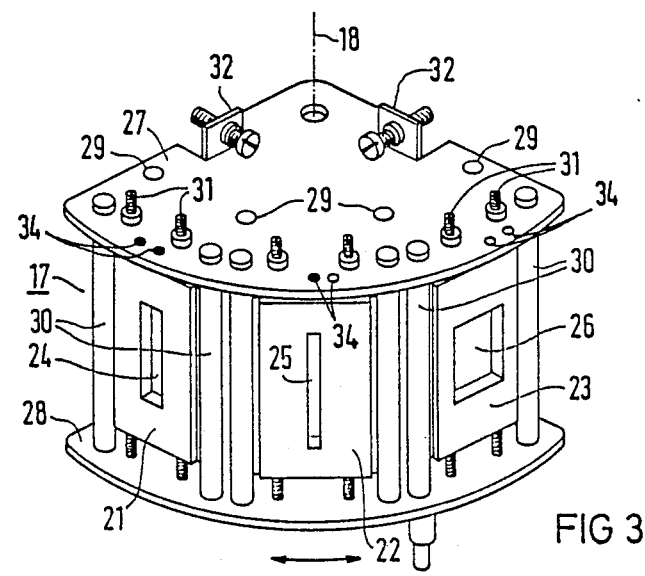
FIG. 3 is an enlarged, perspective view of an embodiment of multiple diaphragm part being utilized in the device of FIG. 1.

The multiple diaphragm part 17, as shown in FIG. 3, is composed of discrete parts and contains three diaphragm inserts 21, 22 and 23, which inserts have apertures 24, 25 and 26 of respectively different sizes and configuration. The size of the diaphragm apertures 24, 25 and 26 correspond to different film cassette formats in the ceph exposure and/or different exposures in a slice exposure. It is to be noted here that even more diaphragm apertures can be provided instead of the three different diaphragm apertures which are shown. In the illustrated embodiment, the two plates 27 and 28 comprising roughly the shape of a circular sector are provided for the acceptance of the diaphragm inserts 21–23, and these plates 27 and 28 are held at a distance from one another by a plurality of perpendicular retaining pins 29. Additional retaining pins 30 are provided in the peripheral region of the plates 27 and 28 for holding the diaphragm inserts, and these additional retaining pins 30 are detachable held by locking rings, not shown, so that a rapid changing of the diaphragm inserts is possible. Adjustment screws 31 can adjust the position of each of the diaphragm inserts relative to the rays so that the beam path of the radiator 16, with which the overall diaphragm arrangement can be exactly aligned. In addition, stop screws, such as 32, can be utilized to limit the amount of rotation around the axis 18.

The multiple diaphragm arrangement contains a sensor arrangement which acquires the momentary position of the multiple diaphragm part 17 and, thus, of the diaphragm apertures 24, 25 and 26, with reference to the radiation source 16. In the present exemplary embodiment, the sensor arrangement is formed by two light barriers 33 (FIG. 2) arranged centrally in the housing 15, which interact with position generators 34 in the form of, for example, depressions, bores or elevations, which are allocated to each of the diaphragm inserts 21-23 and are arranged on the upper plate 27. The position generators 34 have different identifiers, for example, two bores allocated to the diaphragm 23 and only one bore allocated to the diaphragm 22, and no bores allocated to the diaphragm 21, so that the two light barriers 33 can clearly recognize which diaphragm is situated in the beam path of the x-ray source 16.

Figure 4:
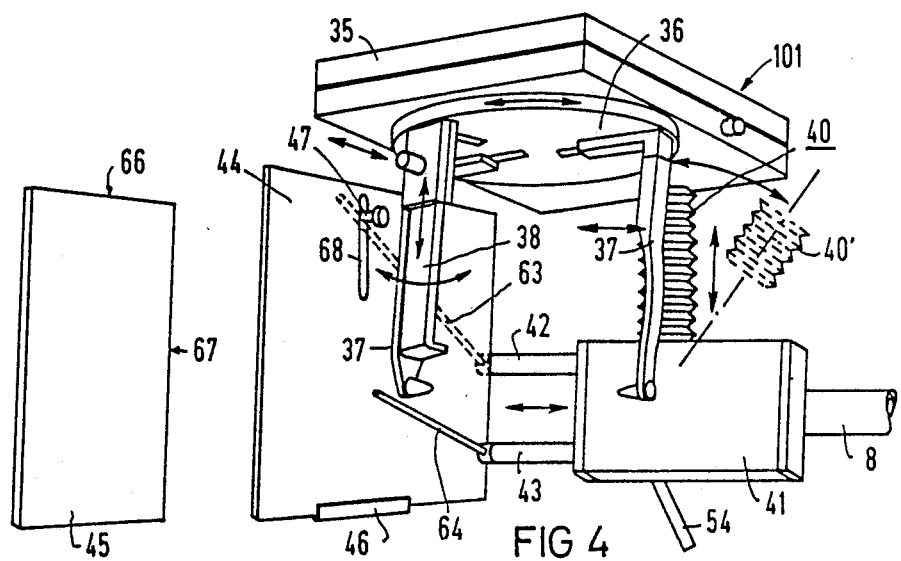
FIG. 4 is a perspective view of a film cassette holder adapted to a head positioning means for producing remote x-ray exposures in accordance with the present invention.
Figure 5:
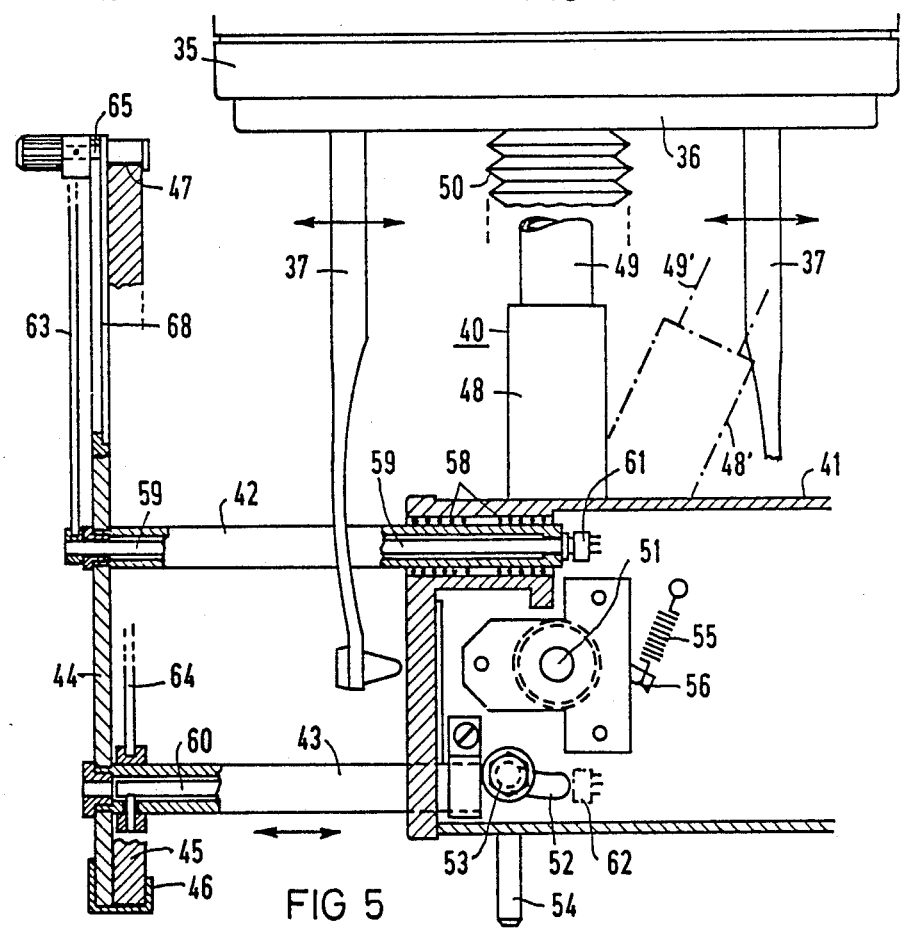
FIG. 5 is a longitudinal cross section of the device of FIG. 4, with portions in elevation for purposes of illustration.

The cassette holding means and head positioning means 101, which are suitable for producing remote x-ray exposures, is schematically illustrated in FIGS. 4 and 5. The means 101 contains a skull holder 35, on which a rotatable dish 36 is mounted for rotation in a known manner around a vertical axis. Two ear button holders or pins 37 are adjustably mounted on the dish 36 for adjustment in the direction of the arrows and lie diametrically opposite one another with respect to the axis of the member 36. A nasion support or nasion supporting part 38 is also arranged on the dish 36 and forms a triangular arrangement with the pins 37 when viewed in the plan view. The nasion support 38 is held on the rotary dish and is adjustable in height and in depth, as indicated by the arrow directions, as well as being pivotable around the journal bearing.

The skull holder 35 is connected to the other end of the carrying pipe 8 by means of a housing 41, which has a vertical mounting means or pipe 40. The housing 41 also supports two horizontal carrying rods 42 and 43, which extend to a film cassette holder 44. The two carrying rods 42 and 43 are held in the housing in an adjustable manner and can be adjusted in the axial direction, as indicated by the arrow. A film cassette 45 containing the x-ray film is inserted into the film cassette holder 44 in an upright position, and the holder 44 has guide elements 46 and 47 for guiding the cassette as it is being inserted.

The tubular mounting means 40, as illustrated in FIG. 5, is composed of two pipes 48 and 49, which are telescoped together and are covered by a shared accordion bellows 50. In order to achieve different extended lengths and, thus, a height adjustment of the skull holder 35 relative to the housing 41, one of the two pipes is provided with a longitudinal channel and the other is provided with a bore, through which a set screw (not shown) engages to enable holding the pipes in the adjusted position. In addition to the height adjustability, which particularly serves the purpose for also imaging the last cervial vertebra in a special exposure, the overall skull holder 35 is also pivotable around a horizontal axis 51 formed by a journal bearing, as indicated by the broken line illustration of the carrier part 40' in FIG. 4, as well as the broken position for the pipes, illustrated at 48' and 49' in FIG. 5. The angle of inclination is limited by a channel or slot 52 in a wall of the housing 41, which receives a threaded bolt 53 that extends through the channel 52 and into the lower end of the telescoping pipe 48. A clamping lever 54 is also screwed on the threaded bolt 53 and enables locking the mounting means for the head holder 35 in the desired angular position.

In order for the skull holder 35 is maintain its basic position when the clamping lever 54 is opened, a tension spring 55 is provided in the housing 41 and is connected, first, to the wall of the housing and, second, to a supporting part 56, which forms a lever arm relative to the rotational axis 51 and is connected to a bushing with a fixed angle.

The two rods 42 and 43 are fashioned as hollow tubular members and are guided by linear bearings 58 in an easy-running fashion in the housing 41. Transmission elements 59 and 60 extend through the tubular members or rods 42 and 43 and one end of each of these transmission elements 59 and 60 is connected to an angle generator in the form of a potentiometer 61 or 62, respectively, and their other end is provided with sensing levers 63 and 64, respectively, which levers are fixed at a predetermined angle. The sensing lever 63 is arranged behind the cassette holder 44 and the sensing lever 64 is positioned in front of the cassette holder 44. The two sensing levers 63 and 64 are part of a sensing arrangement or means, with which the provided film cassette format can be automatically defined and when warranted, displayed at a display after the film cassette is inserted into the film cassette holder 44. The signals are, also, used to control the positioning of a primary diaphragm which belongs to the selected film cassette format into the beam path between the radiation source and subject.

It can be seen from FIG. 5 that the sensing lever 63 is connected, first, to a transmission rod 59, which extends through the film cassette holder 44 and, secondly, is connected by means of an additional cross member 65, which extends through a slot 68 in the film cassette holder 44 to mount the guide 47 against which a top reference surface 66 of the film cassette format is engaged. The free end of the sensing lever 64 lies directly in the path of the cassette 45 and will engage the leading surface 67 to determine the width of the selected film cassette format. The selected film cassette format will define the respective pivoting angles of the two sensing levers 63 and 64 in accordance with the seating of their ends against the reference surfaces 66 and 67. In order for the guide element 47 to adapt to cassette formats differing in height, the cross connection 65 is guided in the vertically extending slot 68 of the holder 44 and is movable along the axis of the lever 63.

Figure 6:
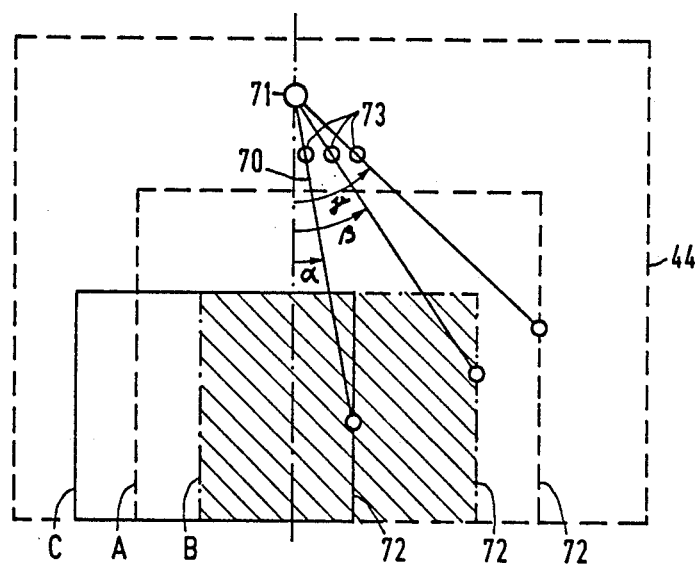
FIG. 6 is a schematic illustration of a modification of a sensor means for acquiring the film cassette format.
Figure 7:
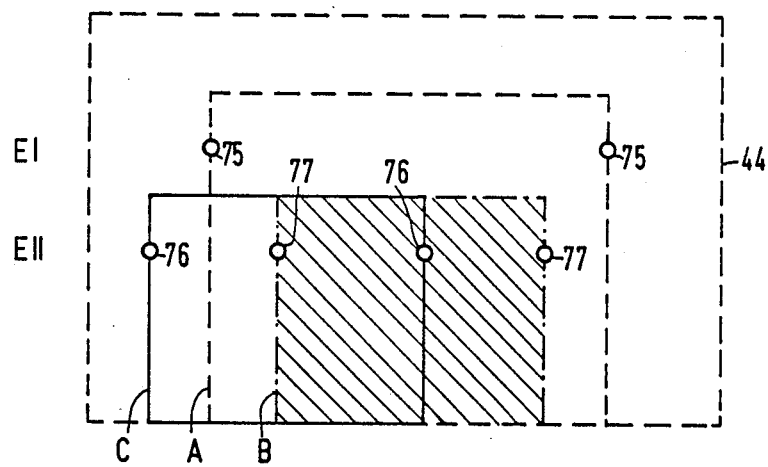
FIG. 7 is a schematic illustration of a second modification of a sensor means for acquiring the film cassette format.

As already mentioned, film cassettes of various sizes can be utilized, for example a cassette like those schematically shown in FIGS. 6 and 7, have a format A (broken lines) comprises the dimensions of 24×30 cm; have the format B (chain lines) comprises the dimension 18×24 cm. In addition, the format C, which also has a size 18×24 cm, but with an asymmetrical arrangement of the cassette relative to the cassette holder in comparison to format B can also be determined.

In the illustrated arrangement of FIGS. 4 and 5, the width of the cassette format is acquired with a sensing lever 64, and the height of the selected film cassette is acquired with the sensing lever 63. A specific film cassette format, accordingly, is defined by a specific pivoting angle of the sensing levers 63 and 64. When a film cassette having a defined format, whether it is the format of A, B or C, is put into place on the holding plate 44, then the film cassette format can be determined by the position of the two sensing levers 63 and 64 in that the analog signals corresponding to the pivoting angles of the sensing levers is generated via the two potentiometers 61 and 62. These analog signals, after appropriate editing and interpretation, either directly indicate the size of the cassette format at the display, such as a display 83 of FIGS. 8 and 9, and/or is provided for the purpose of driving a stepping motor, such as 14, for the multiple diaphragm arrangement shown in FIGS. 2 and 3 so that after the film cassette is inserted, the diaphragm aperture of the primary diaphragm belonging to this film cassette can be automatically brought into the beam path.

An embodiment of the sensor arrangement is shown in FIG. 6, and another embodiment is shown in FIG. 7. In the embodiment of FIG. 6, only one sensing lever 70 is present, and this is pivotably seated in the film holder plate 44 and is connected to a potentiometer 71. In contrast to the previously mentioned embodiment, the sensing lever 70 lies against only one reference surface 72 of the three cassette formats A, B and C, and defines the width of the inserted cassette. The value of the resistance at the potentiometer 71 will identify the pivot position and corresponds to the pivot position having the pivot angles $\alpha$, $\beta$, and $\gamma$, which represent a measure for the selected film format. The acquired analog signal can be digitalized in an analog-to-digital computer and can be displayed in a display. Alternatively and additionally, the signal can be used to drive the adjustment mechanism for the multiple diaphragm part, as shown in the simplified circuit diagram of FIGS. 8 and 9. Since the sensing lever 70 projects into the cassette path in the exemplary embodiment shown here, a material which does not cast a shadow on the film should be selected for the sensing lever.

Instead of the potentiometer 71 for acquiring the angular positions, $\alpha$, $\beta$, and $\gamma$, of the sensing lever 70, it is also conceivable to provide optical sensing elements 73 in, for example, the form of reflector light barriers of light-emitting diodes and photo elements between which the sensing lever moves.

In the second embodiment of FIG. 7, a first sensing pair 75 is provided in a first horizontal plane EI for the largest film cassette format A, which is shown in broken lines. A second pair 76 and third pair 77 are provided in a second plane EII for the film formats B, which is shown in chain lines, and format C, which is shown in bold lines, and have the same height. The sensor pairs 75–77 are arranged at the film cassette holding plate so that they identify the outer limitations of the inserted cassette. As already set forth, the signal acquired from the sensors can be interpreted and can be used for display and/or controlling the drive unit for adjusting the primary diaphragm.

Figure 8:
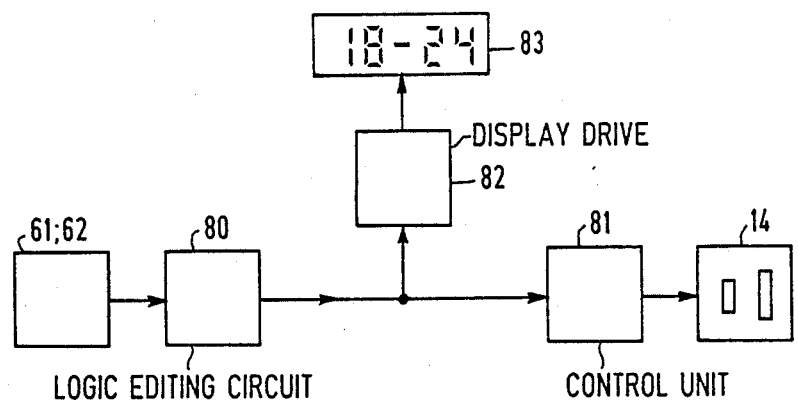
FIG. 8 is a block circuit diagram in accordance with the present invention.
Figure 9:
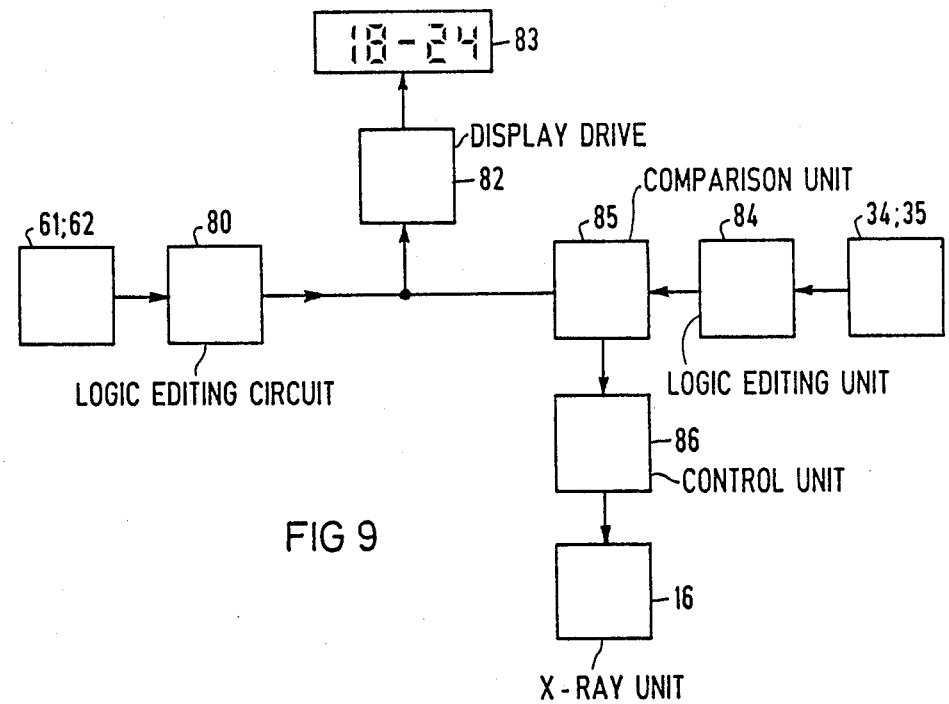
FIG. 9 is a modification of the block circuit diagram of FIG. 8.

A diagramatic illustration of the signal processing arrangement of the present sensor arrangement is illustrated in two embodiments in FIGS. 8 and 9. In the embodiment of FIG. 8, the signals from the sensor 61 and 62, which determine the format of the film cassette, are supplied, first, to a logic editing circuit 80 of conventional design, whose edit signal is then supplied to a control unit 81 for controlling the operation of the adjustment motor 14 (FIG. 2) to position the multiple diaphragm part. In addition, the output from the editing circuit 80 is also supplied to a display drive 82, for instance display driver 7212 INTERSIL which then operates to display the particular format.

In the simplest case, the signal processing via the control unit 81≙86 can be omitted and only the film format corresponding to the film cassette inserted by the operator is displayed at the display. In another case, the correct diaphragm can be immediately positioned into the beam path via the adjustment motor 14 either additionally or alternatively.

In the processing circuits illustrated in FIG. 9, electrical signals from the diaphragm position sensors 34 and 35, shown in FIG. 5, are supplied to a logic editing unit 84, which are conventional means, whose output is then supplied to a comparison unit 85 for instance microcontroller 80C51, SIEMENS that is conventional and compares the output from the logic unit 84 and unit 80 for instance integrated standard circuits (AND or NAND N). When the two signals match, then an interlock of a control unit 86 for instance steppenmotor controller L297, SG5 is disengaged so that the x-ray unit 16 can be utilized. The control unit 86 will maintain the inner lock until there is agreement between the particular diaphragm and film cassette.

Although various minor modifications may be suggested by those versed in the art, it should be understood that we wish to embody within the scope of the patent granted hereon all such modifications as reasonably and properly come within the scope of our contribution to the art.

We claim:

1. In a dental x-ray diagnostics installation comprising a holder, with means for supporting a diaphragm part, said holder being provided between an x-ray source, for providing a radiation beam and a subject for limiting the radiation beam, and a film cassette holder for a film cassette, the improvements comprising said diaphragm part being a multiple diaphragm part with a plurality of diaphragms having different diaphragms apertures for the purpose of changing a film cassette format, said multiple diaphragm part being adjustable by a drive unit, the film cassette holder having sensing means for determining the position and format size of a film cassette inserted into the film cassette holder, a logic circuit for editing a signal from said sensing means to produce an edit signal and means for utilizing the edit signal to perform at least one function selected from a function of displaying information on the format and a function of controlling the operation of the drive unit so that one of the plurality of diaphragm apertures of the multiple diaphragm part can be aligned to a beam path of the x-ray source, said multiple diaphragm part including diaphragm sensing means for determining the particular diaphragm aperture positioned in the path of the beam of radiation, said diaphragm sensing means producing an output signal, said means for utilizing including a comparison logic for receiving the output signal from the diaphragm sensing means and the edit signal from the logic circuit and interlocked means for receiving the output of the comparison logic and stopping operation of said x-ray source until the output of the logic circuit and the diaphragm sensing means coincide.

2. In an x-ray diagnostics installation according to claim 1, wherein the means for utilizing also includes control means for positioning one of the plurality of diaphragms in response to the edit signal of the logic circuit.

3. In an x-ray diagnostics installation according to claim 2, wherein the means for utilizing includes a display being actuated by the edit signal of the logic circuit.

4. In a dental x-ray diagnostics installation comprising a holder, with means for supporting a diaphragm part, said holder being provided between and x-ray source for providing a radiation beam and a subject for limiting the radiation beam, and a film cassette holder for a film cassette, the improvements comprising said diaphragm part being a multiple diaphragm part with a plurality of diaphragms having different diaphragms apertures for the purpose of changing a film cassette format, said multiple diaphragm part being adjustable by a drive unit, the film cassette holder having a vertically positioned plate against which the film cassette is placed, said film cassette holder having sensing means for determining the position and format size of a film cassette inserted into the film cassette holder, said sensing means including a first sensing lever being mounted on the front surface of said plate and having a free end engagable with a first reference edge of the cassette, a second sensing lever being arranged on the back side of said plate and having a sensing element extending through a slot in the plate for engaging a second reference edge of the film cassette, said sensing means including an angle generator means being connected to each of the levers, each angle generator means comprising a potentiometer arranged at the pivot point for the lever to produce signals corresponding to the angular pivot position of the lever, a logic circuit for editing a signal from said sensing means to produce an edit signal and means for utilizing the edit signal to perform at least one function selected from a function of displaying information on the format and a function of controlling the operation of the drive unit so that one of the plurality of diaphragm apertures of the multiple diaphragm part can be aligned to a beam path of the x-ray source.

5. In an x-ray diagnostics installation according to claim 4, wherein each of the levers is mounted by a mechanical bearing on the plate.

6. In an x-ray diagnostics installation according to claim 5, wherein each of the levers is connected to a transmission rod at a rigid angle so that rotation of said lever rotates said rod, each of said rods at an end opposite the connection to its lever being connected to the potentiometer.

* * * * *